United States Patent
Marion et al.

(10) Patent No.: US 9,073,803 B2
(45) Date of Patent: Jul. 7, 2015

(54) METHOD FOR PRODUCING HYDROCARBONS WITH CONTINUOUS CHARGING OF THE CATALYST

(71) Applicant: IFP ENERGIES NOUVELLES, Rueil-Malmaison Cedex (FR)

(72) Inventors: Marie Claire Marion, Vernaison (FR); Fabrice Diehl, Lyons (FR); Francois Hugues, Vernaison (FR)

(73) Assignee: IFP ENERGIES NOUVELLES, Rueil-Malmaison Cedex (FR)

( * ) Notice: Subject to any disclaimer, the term of this patent is extended or adjusted under 35 U.S.C. 154(b) by 256 days.

(21) Appl. No.: 13/713,234

(22) Filed: Dec. 13, 2012

(65) Prior Publication Data
US 2013/0178545 A1 Jul. 11, 2013

(30) Foreign Application Priority Data

Dec. 14, 2011 (FR) ..................................... 11 03861

(51) Int. Cl.
| | |
|---|---|
| *C07C 27/00* | (2006.01) |
| *B01J 20/34* | (2006.01) |
| *C07C 1/04* | (2006.01) |
| *B01J 37/16* | (2006.01) |
| *B01J 37/18* | (2006.01) |
| *C10G 2/00* | (2006.01) |
| *B01J 23/75* | (2006.01) |
| *B01J 23/89* | (2006.01) |

(52) U.S. Cl.
CPC ............... *C07C 1/0445* (2013.01); *B01J 37/16* (2013.01); *B01J 37/18* (2013.01); *B01J 23/75* (2013.01); *C10G 2/332* (2013.01); *B01J 23/8913* (2013.01)

(58) Field of Classification Search
CPC ......... C10G 2/332; B01J 21/08; C07C 27/06; C07C 27/04
USPC ......................... 518/700, 715; 502/20, 34, 53
See application file for complete search history.

(56) References Cited

U.S. PATENT DOCUMENTS

| | | |
|---|---|---|
| 2003/0144130 A1 | 7/2003 | Clark et al. |
| 2003/0144367 A1 | 7/2003 | Jacobus Van Berge et al. |
| 2007/0135527 A1 | 6/2007 | Maretto et al. |
| 2012/0071571 A1* | 3/2012 | Abbas et al. .................. 518/700 |
| 2012/0302433 A1* | 11/2012 | Peat et al. ..................... 502/100 |

FOREIGN PATENT DOCUMENTS

WO    WO 2010/049715 A1    5/2010

OTHER PUBLICATIONS

Search Report of FR 1103861 (Jun. 6, 2012).

* cited by examiner

*Primary Examiner* — Jafar Parsa
(74) *Attorney, Agent, or Firm* — Millen, White, Zelano & Branigan, P.C.

(57) ABSTRACT

The present invention relates to a method for the continuous production of hydrocarbons from synthesis gas in the presence of a catalyst comprising a synthesis step in which a synthesis gas is reacted in the presence of a catalyst in a Fischer-Tropsch synthesis reactor (4),
characterised in that, at the same time as the synthesis step, the following successive steps are carried out:
a) charging a catalyst precursor comprising cobalt oxide in a reduction reactor (2);
b) reducing the catalyst precursor charged in step a) by placing it in contact with a reduction gas comprising hydrogen ($H_2$) and/or carbon monoxide (CO); and
c) introducing the catalyst reduced in step b) into the synthesis reactor (4).

16 Claims, 1 Drawing Sheet

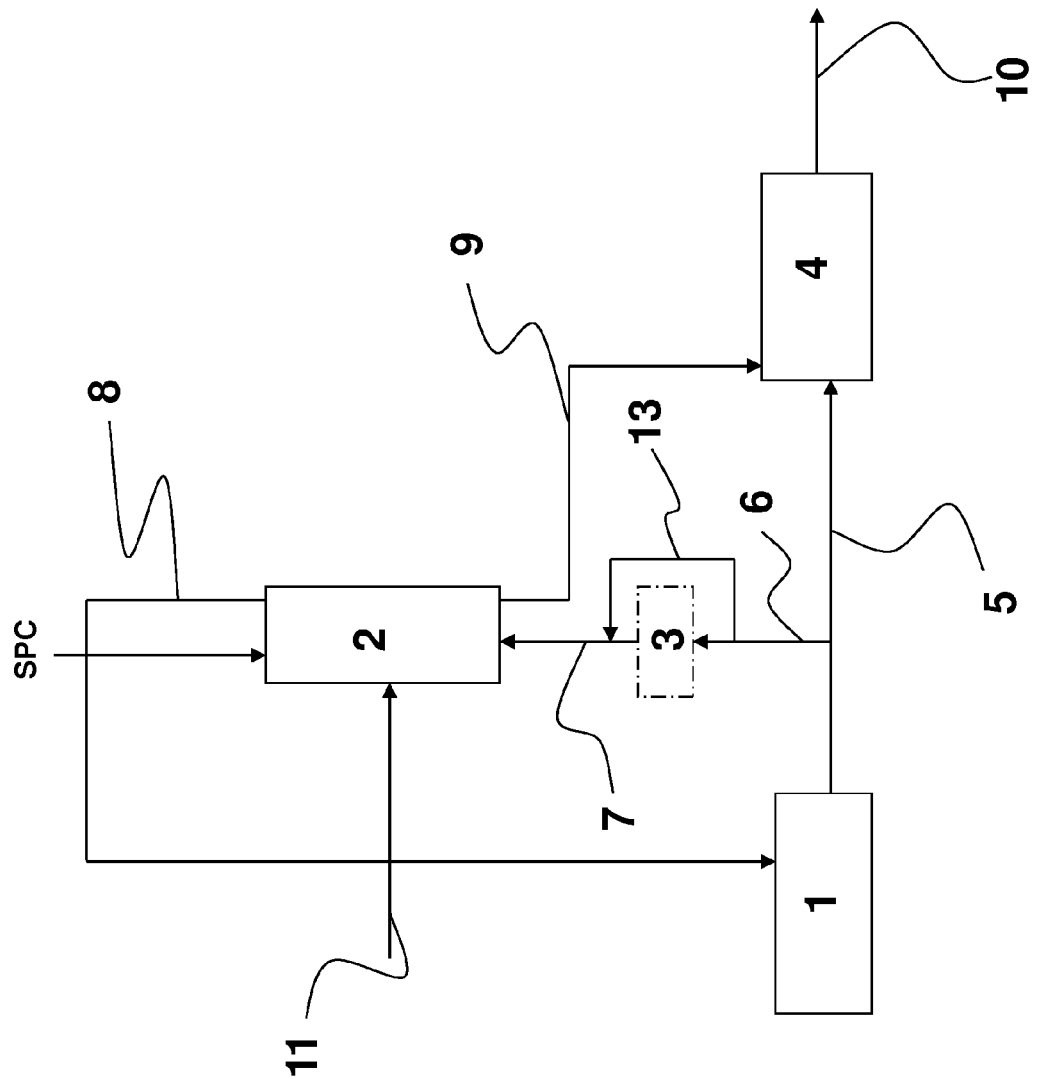

METHOD FOR PRODUCING HYDROCARBONS WITH CONTINUOUS CHARGING OF THE CATALYST

The invention relates to a method for producing hydrocarbons. In particular, the production method is a Fischer-Tropsch method for synthesis of hydrocarbons from synthesis gas.

PRIOR ART

The synthesis of hydrocarbons from an admixture constituted by CO and $H_2$, more commonly known as synthesis gas, has been known for some time. It is possible to mention in particular the work of F. Fischer and H. Tropsch who, since 1923, have given their name to this chemical conversion, well known as Fischer-Tropsch synthesis. Fischer-Tropsch synthesis (FT) is a reaction which allows paraffin-based, olefin-based liquid hydrocarbons and/or oxygenated derivatives to be synthesised from synthesis gas, which is itself obtained from natural gas, carbon or biomass. This reaction, used on an industrial scale in Europe during the Second World War and also in South Africa since the 1950s, has seen a spectacular resurgence in interest since the 1980s-1990s following the developments with respect to the cost of petroleum and gas, but also for environmental reasons. It is possible to mention, for example, that numerous GTL "gas to liquid" projects are currently being implemented, for example, in Qatar.

Fischer-Tropsch synthesis (FT) is also a means for utilising natural gas and allows, inter alia, some diesel fuels of very good quality and without sulphur to be produced from natural gas.

A number of metals can be used in order to catalyse this reaction, including cobalt (Co) and iron (Fe). The catalyst is generally prepared by means of impregnation of a support (for example, a support based on alumina, silica or silica-alumina, etc.) from a metal precursor, such as a nitrate or an acetate of the metal. There is obtained, after one or more steps for drying and calcination, the catalyst, said to be "in oxide form", also referred to as the "oxide precursor of the catalyst" which comprises the metal oxide supported on the support.

Given that the Fischer-Tropsch synthesis is catalysed by the metal and not the oxide, one ought then to reduce the precursor of the catalyst in order to convert the metal oxide (for example, $Co_3O_4$) into the metal phase (Co(0)).

Generally, the reduction of the catalyst precursor is carried out in a dedicated unit, under a gaseous atmosphere in the presence, for example, of hydrogen. After this reduction phase, the catalyst is preferably protected from the air in order to prevent the reoxidisation thereof and thus to retain the active metal phase in its current state. One of the methods used industrially in order to protect the reduced catalyst during its storage and its transport until charging in the FT unit is a process for coating the reduced catalyst under paraffin. Under temperature conditions which are adequate for the paraffins to be in the liquid phase (generally between 50 and 200° C.), the reduced catalyst is mixed with this liquid. After cooling to ambient temperature, the catalyst is coated and protected, in particular from air, by the solidified paraffins. These steps (reduction and coating) are costly (cost of the coating paraffins, unit cost of each operation). Furthermore, the coating step increases the volume of the catalyst and this brings about an excessive cost in terms of transport.

Document EP 593 522 is known and describes a method for activation or reactivation of a catalyst based on cobalt in which the oxidised catalyst (or catalyst precursor) is reduced in the presence of a reduction gas comprising carbon monoxide (CO) and optionally hydrogen ($H_2$) which must be present in a quantity of less than 30% by volume of hydrogen.

This same document discloses a process for starting an FT synthesis unit which implements an in situ reduction of the catalyst. This method comprises the following successive steps:

i) reducing, in the actual Fischer-Tropsch synthesis reactor, the catalyst precursor containing cobalt at a high temperature with a gas containing carbon monoxide, this gas containing less than 30% by volume of hydrogen based on the volume of carbon monoxide;

ii) passing a synthesis gas over the reduced catalyst, at a temperature which is at least 10° C. greater than the maximum temperature reached during the subsequent step carried out under Fischer-Tropsch conditions; and iii) passing the synthesis gas over the catalyst under the conditions of the Fischer-Tropsch method in the Fischer-Tropsch synthesis reactor.

It has further been found that, during the FT synthesis, a portion of the catalyst and/or the active metal can be carried in the hydrocarbon phase formed, following phenomena of attrition or dissolution or the catalyst itself de-activates.

It is therefore necessary to regularly add "fresh" catalyst in order to maintain the productivity of the unit. So that the FT method is industrially viable, the stopping of the installation, for example, in order to add the catalyst, must be done as infrequently as possible. Any interruption of the unit is complex and costly in terms of time and therefore money.

The method disclosed in EP 593 522, which implements an in situ reduction of the catalyst precursor directly in the FT synthesis reactor is therefore not a solution to the problem of providing a method for which stoppages, in particular for the supply of catalyst, are less frequent and which is rapidly "operational" after a stoppage.

SUMMARY OF THE INVENTION

An object of the invention is to provide a method for hydrocarbon synthesis which is more advantageous from the point of view of controlling the flow of materials (for example, transport, storage) and less costly to implement, in particular by avoiding an ex situ reduction of the catalyst and therefore the step of protecting the catalyst once reduced.

Another object of the invention is to provide a method for which the supply of reduced catalyst does not require complete stoppage of the FT reactor or an interruption of the production.

To this end, there is proposed a method for the continuous production of hydrocarbons from synthesis gas in the presence of a catalyst comprising a synthesis step in which a synthesis gas is reacted in the presence of a catalyst in a Fischer-Tropsch synthesis reactor, characterised in that, at the same time as the synthesis step, the following successive steps are carried out:

a) charging a catalyst precursor comprising cobalt oxide in a reduction reactor;

b) reducing the catalyst precursor charged in step a) by placing it in contact with a reduction gas comprising hydrogen ($H_2$) and/or carbon monoxide (CO); and c) introducing the catalyst reduced in step b) into the synthesis reactor.

In the context of the invention, the "catalyst precursor" may comprise, in addition to the cobalt oxide, one or more other metals or mixed oxide which act as promoting elements, but this term also refers to a phase which comprises the oxide mentioned above and which is supported on a catalyst support.

In this manner, according to the invention, the step of reduction of the catalyst precursor is integrated in situ with the FT synthesis method itself, which allows the catalyst precursor to be reduced and activated at the actual site of the FT synthesis unit and therefore elimination of the costs involved in the protection, the storage and the transport of the reduced catalyst. Furthermore, the reduction is carried out in a reactor which is dedicated to this purpose; this has the advantage that it is no longer necessary to stop the FT synthesis reactor in order to provide a source of "fresh" activated catalyst, in contrast to the method disclosed in document EP 593 522.

Another object of the invention is to provide a method for which the starting is facilitated and for which the duration of the transient starting phase is limited to the greatest possible extent.

To this end, the method further includes the following steps:

d) charging a useful quantity Q of the catalyst precursor in the oxidised state in the reduction reactor;

e) reducing the total quantity Q of the catalyst precursor in the oxidised state charged in step d) in the presence of a reduction gas comprising carbon monoxide and/or hydrogen;

f) charging the total quantity Q of the catalyst reduced in step e) in the Fischer-Tropsch synthesis reactor.

In this manner, in accordance with the method, it is also possible to activate in advance a useful quantity of catalyst with a view to an imminent stoppage (for example, for maintenance) whilst continuing to operate the synthesis unit until the last moment with the stoppage; in this instance, there is again a reserve of "fresh" reduced catalyst for the subsequent restarting operation.

Another object of the invention is to provide a method whose starting is facilitated in particular by reducing to the greatest possible extent the time required for the catalytic activity of the catalyst to reach a value which is referred to as stationary and which corresponds to that encountered under stationary conditions of FT synthesis. To this end, the method further includes a step for conditioning the reduced catalyst from step b) or e) in the presence of a gas comprising CO alone or an admixture of CO/$H_2$ before it is charged in the Fischer-Tropsch synthesis reactor.

This conditioning step may involve placing the reduced catalyst in contact with a reduction gas which comprises an optimised admixture comprising hydrogen ($H_2$) and carbon monoxide (CO), under adequate temperature and pressure conditions. For example, the conditioning of the reduced catalyst can be carried out under a non-modified synthesis gas from the same source of synthesis gas which supplies the FT synthesis reactor.

Advantageously, it is possible to use the reduction reactor as the conditioning reactor of the catalyst which has already been reduced in order to form the "true FT catalyst" as described in particular by H. Schulz (Catal. Today 71, 2002, 351-360).

The true catalyst is the one which operates in the FT synthesis reactor. The FT catalyst finishes its construction under synthesis gas under the conditions of the method. During this construction end phase, the activity of the FT catalyst is modified. The conditioning step therefore allows the construction of the FT catalyst to be completed in advance so that it can be used in the FT synthesis reactor which operates under stationary conditions.

It is also possible to carry out this conditioning step in a dedicated chamber which is different from the reduction reactor and the FT synthesis reactor.

This conditioning of the reduced catalyst can also be carried out in several phases. For example, the reduced catalyst is subjected to a first conditioning phase under synthesis gas having a first molar ratio $H_2$/CO and then a second phase under synthesis gas having a molar ratio $H_2$/CO different from the first ratio. Of course, the person skilled in the art is able to adapt the number of phases and the conditioning parameters (for example, the composition of the reduction gas, temperature, the total pressure) in accordance with the type of catalyst and the reduction process implemented in step b) or e).

Advantageously, the conditioning reduction gas is a synthesis gas (that is, which comprises a CO/$H_2$ admixture) which originates directly from the same synthesis gas source which supplies the FT reactor and whose molar ratio $H_2$/CO is between 0.01 and 10.

Preferably, the operating parameters of the conditioning step will be determined so as to also bring about a change in structure of the active phase, for example, a transition from the crystalline phase of cobalt to the compact hexagonal phase.

Alternatively, the conditioning of the catalyst is implemented in the presence of a reduction gas which comprises only CO.

According to a preferred embodiment of the method, the precursor of the catalyst is first reduced under $H_2$ alone, then is processed under synthesis gas which has a molar ratio $H_2$/CO which is between 0.1 and 0.5 and is finally subjected to a second conditioning phase under synthesis gas having a molar ratio $H_2$/CO of between 1 and 2.5. The second conditioning phase is preferably carried out with a synthesis gas whose ratio $H_2$/CO is similar to that encountered in the FT synthesis reactor (that is to say, whose ratio $H_2$/CO is between 1 and 3).

According to another preferred embodiment, the oxide catalyst precursor is first reduced in the presence of a reduction gas which comprises only $H_2$, then is processed in the presence of a gas which comprises only CO. This catalyst is then processed with a gas which comprises the admixture CO and $H_2$ such that the molar ratio $H_2$/CO is between 2 and 10. Finally, this solid is subjected in a final phase to a synthesis gas whose molar ratio $H_2$/CO is similar to that encountered in the FT synthesis reactor (that is to say, whose ratio $H_2$/CO is between 1 and 3).

According to another preferred embodiment, the catalyst precursor is first reduced in the presence of a synthesis gas which comprises an admixture of $H_2$ and CO such that the molar ratio $H_2$/CO is greater than 1. Subsequently, the reduced catalyst is processed during a first phase in the presence of a synthesis gas comprising an admixture of $H_2$ and CO such that the molar ratio $H_2$/CO is less than 1. This solid is finally subjected to a second conditioning phase in the presence of a synthesis gas whose molar ratio $H_2$/CO is similar to that encountered in the FT synthesis reactor (that is to say, whose ratio $H_2$/CO is between 1 and 3).

According to the invention, the supply of the catalyst to the Fischer-Tropsch synthesis reactor can be carried out either in semi-continuous mode or in continuous mode.

Preferably, the supply of reduced (or reduced and processed) catalyst is carried out in a semi-continuous manner. In this operating method, only a portion of the catalyst which has been activated (reduced or reduced and processed) is conveyed to the FT reactor. The remaining portion of the activated catalyst is kept under optimal activation/ conditioning conditions and can be used as a source of fresh catalyst for one or more subsequent replenishment operations.

Advantageously, the reduction gas advantageous for the reduction of the catalyst precursor comprises only hydrogen (or in admixture with an inert gas) or only carbon monoxide (or in admixture with an inert gas) or a synthesis gas which has a molar ratio $H_2/CO$ of between 0.01 and 10.

If the reduction gas is carbon monoxide alone or an $H_2$ and CO admixture, this gas may originate from the source of synthesis gas which is used for the FT synthesis and whose molar ratio $H_2/CO$ has been modified before it is supplied to the reduction reactor. For example, the processing of the synthesis gas can be carried out using a device for membrane separation in the gas phase which allows the synthesis gas to be enriched with CO.

In the context of the invention, the reduction is carried out at a temperature between 200 and 500° C., at a total pressure between 1 and 50 bar and under a gas flow between 0.1 and 20 Nl/h/g of catalyst to be processed.

In accordance with the invention, the catalyst precursor is cobalt oxide optionally incorporating one or more metals or metal oxide(s), known as "promoters", selected from Cu, Mn, Ru, Pd, Pt, Re, La.

According to the invention, the cobalt oxide is supported by a support which comprises one or more oxides of a metal selected from Al, Si, Ti, Zr, Ce, Cu, Zn, Ni. It is possible to mention as a support silica, alumina, silica-alumina, titanium oxide or zirconia alone or in admixture.

BRIEF DESCRIPTION OF THE FIGURES

These aspects and other aspects of the invention will be clarified in the detailed description of specific embodiments of the invention given by way of example, reference being made to the single Figure, in which:

FIG. 1 is a schematic illustration of the method according to the invention.

DETAILED DESCRIPTION OF SPECIFIC EMBODIMENTS

FIG. 1 is a schematic illustration of a unit for the production of a hydrocarbon by means of Fischer-Tropsch type synthesis which comprises:
 a source 1 of synthesis gas which comprises as principal constituents hydrogen ($H_2$) and carbon monoxide (CO);
 a reduction reactor 2 which is supplied with FT catalyst precursor (catalyst in the oxidised state) from a source of SPC catalyst precursor (not illustrated);
 a processing unit 3 for the synthesis gas (this processing unit 3 being optional);
 an FT synthesis reactor 4.

As illustrated in FIG. 1, the source 1 of synthesis gas supplies the synthesis reactor 4 via a supply pipe 5.

A pipe 6 allows a portion of the synthesis gas to be conveyed from the source 1 to the processing unit 3. In the present example, the pipe 6 is connected to the supply pipe 5. However, it is possible to directly connect the pipe 6 of the synthesis gas source 1.

The synthesis gas processing unit may be, for example, a device for gas/gas membrane separation which allows the synthesis gas to be enriched with carbon monoxide CO. In this manner, at the output of the processing unit 3, the reduction gas has a molar ratio $H_2/CO$ of between approximately 0 and 10, preferably between 0.05 and 3, even more preferably between 0.1 and 1.

The pipe 13 is a branch pipe which allows the reduction reactor 2 to be supplied with synthesis gas without modifying the composition thereof.

From the processing unit 3 extends a pipe 7 which is intended to supply the reduction reactor 2 with reduction gas whose composition has been changed.

If the reduction of the catalyst precursor is carried out under hydrogen, the reactor 2 is supplied with $H_2$ gas (optionally diluted in an inert gas) via the pipe 11 which itself is connected to a source of hydrogen (not illustrated).

In the context of the invention, the catalyst precursor preferably comprises cobalt oxide and a support based on silica, alumina or silica-alumina, zirconia, titanium oxide or any other support comprising one or more of the elements selected from Al, Si, Ti, Zr, Ce, Co, Cu, Zn, Ni. The catalyst precursor may also comprise one or more metals which act as a promoter. By way of example, the metal or the metals may be selected from Cu, Mn, Ru, Pd, Pt, Re, La.

When the catalyst precursor comprises cobalt oxide and a support, it may be obtained by means of a method which involves one or more step(s) for impregnating the precursor of the metal on the support (for example, cobalt nitrate), followed by a step of drying and finally a step of calcination as taught in document EP 527 032. This step of calcination is intended in particular to decompose the metal precursor and form the metal oxide.

The catalyst precursor (cobalt in the oxide state), which is a solid, is placed in contact with a reduction gas, for example, in a reactor 2 of the fluidised bed, cross-flow fixed bed or expanded bed type, or in a counter-current reactor or in a slurry type reactor.

The operating conditions for the reduction are preferably as follows:
 temperature: between 200 and 500° C., preferably between 200° C. and 450° C., even more preferably between 230 and 400° C.;
 total pressure: between 0.1 MPa and 5 MPa, preferably between 0.1 MPa and 3 MPa;
 rate of the gas flow in relation to the mass quantity of the catalytic solid processed: between 0.1 and 20 Nl/h/g, preferably between 1 and 10 Nl/h/g;
 duration: between 1 and 24 hours, preferably between 1 and 10 hours, preferably between 2 and 6 hours.

The person skilled in the art is able to optimise the reduction operating conditions in accordance with the type of catalyst used.

As illustrated in FIG. 1, the effluent reduction gas is discharged from the reduction reactor 2 via a pipe 8 and may optionally, after processing, be partially returned to the source of synthesis gas 1 or be partially recycled to the unit 3 or the reduction reactor 2.

The catalyst in the reduced state is itself drawn from the reduction reactor 2 and is conveyed towards the FT synthesis reactor 4 by means of the pipe 9.

The FT synthesis reaction is carried out in the reactor 4 under conventional operating conditions, that is to say,
 temperature: 200-250° C.
 total pressure: 1-4 MPa
 molar ratio $H_2/CO$: 1 to 3

The hydrocarbons from the FT reaction are removed from the synthesis reactor via the pipe 10. A portion of the products formed in the reactor 4 is generally converted by means of hydroprocessing (hydrocracking and hydro-isomerisation) in order to produce in particular fuels.

The operation of a production unit implementing the method according to the invention will be described below.

A) Starting Phase of the Unit

There is charged into the reduction reactor 2 a useful quantity Q of the precursor of the catalyst for an FT synthesis in the reactor 4. At the same time or afterwards, the unit 1 for the production of synthesis gas is started.

The useful quantity Q of the catalyst precursor is then reduced. To this end, there is introduced into the reactor 2 a reduction gas which is either the same synthesis gas as that of the source 1 via the pipes (6, 13, 7), or a synthesis gas which has previously been subjected to an enrichment operation which practically enables a flow to be achieved which is free from one of the 2 constituents (for example, a flow containing CO free from $H_2$) via the pipes (6, 7). However, for economic reasons, if a reduction under hydrogen is envisaged, it is more advantageous to use an external source of hydrogen which supplies the reactor 2 via the pipe 11.

The reactor 2 is then brought into optimal conditions for the reduction of the catalyst precursor. The reduction can be optimised by acting on various control variables, such as the temperature profile, the pressure, the reduction gas flow rate.

After the reduction of the catalyst is complete, the total useful quantity Q is introduced into the reactor 4 and the FT synthesis reaction itself is started whilst the reduced catalyst supply pipe 9 is closed.

Optionally, before it is introduced into the FT reactor, the reduced catalyst is subjected to a conditioning phase which involves processing the catalyst in the presence of a synthesis gas in accordance with a method which may comprise a plurality of successive steps which involve different parameters, such as the purity of the synthesis gas, the molar ratio $H_2/CO$ of the synthesis gas, the temperature and the pressure.

Typically, the operating parameters of the conditioning step are as follows:
- Temperature: 200-500° C., preferably 200-300° C.;
- Pressure: from 0.1 to 5 MPa, preferably from 1 to 4 MPa;
- Molar ratio $H_2/CO$: from 0 to 10
- Purity of the synthesis gas between 10 and 100%;
- GHSV: 0.1 to 20 Nl/h/g, preferably between 1 and 10 Nl/h/g;
- Duration: between 1 and 48 hours, preferably between 2 and 24 hours, preferably between 2 and 15 hours.

B) Hydrocarbon Production Phase

After starting the synthesis, the reduction reactor 2 is again supplied with catalyst precursor and reduction gas in order to prepare "fresh" activated catalyst which will be used afterwards to supply the FT reactor 4 during the period of continuous operation of the reactor 4.

Preferably, after being reduced, the catalyst is subjected to a conditioning phase in which it is processed in the presence of a synthesis gas in accordance with a procedure which implements one or more operating conditions. This conditioning phase is carried out in the reduction reactor 2 or in another chamber which is dedicated to this conditioning phase and which is different from the reactor 2 and the synthesis reactor 4.

After this conditioning phase, the catalyst is conveyed to the synthesis reactor 4 which is kept in an operational state. This is referred to as make-up of catalyst which is carried out without interrupting the Fischer-Tropsch synthesis reaction.

In a Fischer-Tropsch method, it is possible to observe a reduction of activity and productivity either owing to loss of catalyst owing to the attrition thereof (and transport of catalyst fines) with the output of the products formed, or owing to deactivation of the catalyst over time. In this manner, in order to maintain the productivity of the unit at its best level, it is necessary to add fresh catalyst in order to compensate for material and/or activity losses of the catalyst.

Owing to the method according to the invention, this addition is carried out directly from the reduction and/or conditioning reactor, either in continuous mode or in semi-continuous mode (per batch) without requiring even a temporary stoppage of the synthesis unit. Furthermore, the reduction/conditioning conditions are optimised in order to form a reduced and processed catalyst whose catalytic activity is already capable of operating under the operating conditions encountered in the FT synthesis reactor, that is to say, a catalyst which is directly "ready to use".

To summarise, the method and the production unit according to the invention afford the following advantages:
- less cost in terms of controlling the flow of materials since the reduction of the catalyst precursor is carried out at the actual site of the synthesis unit, optionally with a source of reduction gas which is the same as that used for the FT synthesis and which is permanently available;
- providing an active and reduced catalyst under optimal conditions, which has improved catalytic performance levels and which has not been subjected to storage or protection processes;
- providing at all times a catalyst which has been reduced and processed under optimal and controlled conditions and which is directly ready to use for carrying out the Fischer-Tropsch synthesis and which reduces (or even eliminates) the transient start-up or make-up phases;
- providing an FT synthesis unit whose make-up operations for "fresh" catalyst do not require an interruption of the Fischer-Tropsch reaction or a stoppage of the unit and which are carried out with the catalyst being preserved.

EXAMPLE 1

A test was carried out in a pilot installation based on the schematic illustration of FIG. 1. The catalyst precursor is a cobalt oxide which is supported on a Siralox® support (alumina stabilised with Si and marketed by Sasol). The content of cobalt is 13% by weight relative to the total weight of the catalyst precursor.

30 g of catalyst precursor are charged into the reduction reactor and are subjected to four successive processing operations, that is to say, under $H_2$, then under CO, and finally under synthesis gas in a molar ratio $H_2/CO$ of 7 then 2. The conditions are set out in the following Table 1:

TABLE 1

| | Processing operation | | | |
|---|---|---|---|---|
| | N°1 (reduction) | N°2 (conditioning operation 1) | N°3 (conditioning operation 2) | N°4 (conditioning operation 3) |
| Reduction gas | $H_2$ | CO (admixture $CO/N_2$) | $H_2$ + CO | $H_2$ + CO |
| T (° C.) | 400° C. | 200° C. | 230° C. | 230° C. |
| P (MPa) | 0.1 | 3 | 2 | 2.6 |
| GHSV (Nl/h/g) | 2.5 | 2 | 5 | 5 |
| Purity of the reduction gas (% vol) | 100 | 10 (10/90) | 100 | 70% |
| Ratio $H_2/CO$ | — | — | 7 | 2 |
| Duration | 4 hours | 24 hours | 8 hours | 2 hours |

Following these reduction and conditioning operations, the catalyst activated in this manner is transferred into the Fischer-Tropsch synthesis reactor (FT) of the slurry type, charged beforehand with a paraffinic solvent (octadecane) and brought to 120° C.

After charging the catalyst, the synthesis gas (dilution 30%, molar ratio $H_2/CO=2.0$) is introduced into the FT synthesis reactor. The pressure is brought to 26 bar and the temperature is brought to 230° C. in accordance with an increase of 50° C./hour up to 200° C. then 10° C./hour between 200 and 230° C.

The FT synthesis reaction is carried out in a continuous manner under the following conditions: 26 bar, 230° C., with a supply of synthesis gas diluted to 30% in $N_2$ (purity of the synthesis gas 70%) and characterised by a molar ratio $H_2/CO$ of 2.0 (or composed of ⅓ of CO and ⅔ of $H_2$). The flow rate of synthesis gas is regularly adjusted in order to maintain the conversion rate of CO at 56%.

In parallel with the operation of the Fischer-Tropsch synthesis reactor, a new batch of catalyst is prepared in the reduction reactor by following the same procedure as for the first batch prepared (cf. Table 1): 3 g of catalyst precursor are charged into the reduction reactor and are subjected to four successive processing operations described in Table 1.

After 30 days of synthesis, this second batch of catalyst is transferred into the Fischer-Tropsch synthesis reactor during operation by bringing about a pressure difference between the two reactors. This addition of catalyst during operation of the Fischer-Tropsch synthesis reactor allows its level of activity and its productivity to be increased again: the addition of "fresh" catalyst allows the charge flow rate to be increased again and this allows the production of Fischer-Tropsch hydrocarbons to be increased.

The catalyst performance levels are monitored over time (Table 2)

TABLE 2

| Time (day) | Charging or addition of catalyst (g) | T (° C.) | P (MPa) | Flow rate of synthesis gas (Nl/h) | Conversion of CO (%) | Production of C5+ (g/h) |
|---|---|---|---|---|---|---|
| 0 | 30 | 230 | 2.6 | 150 | 47.8 | 6.9 |
| 1 | — | 230 | 2.6 | 120 | 56.1 | 6.5 |
| 8 | — | 230 | 2.6 | 104 | 56.2 | 5.6 |
| 15 | — | 230 | 2.6 | 98 | 56.0 | 5.3 |
| 29 | — | 230 | 2.6 | 95 | 56.2 | 5.1 |
| 30 | 3 | 230 | 2.6 | 104 | 56.3 | 5.6 |

At the beginning, the catalyst has a transient temporary excessive activity which can be seen in a high level of productivity (C5+>6 g/h).

After 8 days of operation, the system has reached its stationary mode with C5+ production values which are almost stable. Between the $8^{th}$ and the $30^{th}$ day of operation, the flow rate of synthesis gas is adjusted in order to maintain a conversion level of CO of approximately 56%. During this period, it is possible to consider that the system is in stationary mode since the variation of the flow rate (at a constant CO conversion level) is weaker and less frequent than in relation to the first eight days.

After one month, there is observed a slight decrease in the production of C5+ which changes from 5.6 to 5.1 g/h. An addition of catalyst is carried out on the $30^{th}$ day. It may be noted that the value of the production parameter C5+ increases rapidly to return to a value which corresponds to that found after 8 days of operation.

This example illustrates in a specific manner the operation of an industrial unit which operates at constant capacity.

EXAMPLE 2

A) Reduction and Conditioning of a Catalyst According to the Invention

A test was carried out in a pilot installation based on the schematic illustration in FIG. 1. The catalyst precursor is a cobalt oxide which is promoted by ruthenium and which is supported on a Puralox® support (of the alumina type marketed by Sasol). The catalyst thus contains 11% by weight of cobalt and 0.2% by weight of ruthenium relative to the weight of the catalyst precursor.

30 g of catalyst precursor are charged in the reduction reactor and are subjected to a processing operation under synthesis gas, the conditions of which are set out in Table 3 below:

TABLE 3

| Processing operation | N°1 |
|---|---|
| Reduction gas | $H_2$ + CO |
| T (° C.) | 230° C. |
| P (bar) | 30 |
| GHSV (Nl/h/g) | 0.6 |
| Purity of the reduction gas (% vol) | 100 |
| Ratio $H_2/CO$ | 2.0 |
| Duration | 24 hours |

Following this reduction processing operation, the catalyst activated in this manner is transferred into the Fischer-Tropsch synthesis reactor (FT) of the slurry type, charged beforehand with a paraffinic solvent (octadecane) and brought to 230° C. Before the catalyst is charged, the synthesis gas having a ratio $H_2/CO$ of 2.0 is introduced into the FT synthesis reactor. The pressure is brought to 20 bar. The FT synthesis reaction is then carried out continuously under the following conditions: 20 bar, 230° C., with a supply of pure synthesis gas of 120 Nl/h and whose $H_2/CO$ ratio is 2.0. The catalytic performance levels are monitored over time (Table 2).

B) Comparative Example

The catalyst precursor (30 g) used in example A) is reduced in conventional manner, in the presence of hydrogen, in a dedicated installation (ex situ) at 350° C. for 8 hours.

After reduction, the reduced catalyst is charged in the Fischer-Tropsch synthesis reactor and tested under the same conditions as in example A), that is: 20 bar, 230° C., with a supply of pure synthesis gas, ratio $H_2/CO$ of 2.0, flow rate 120 Nl/h. The catalytic performance levels are measured over time (Table 4).

TABLE 4

| Performance levels of the catalysts A and B | | | |
|---|---|---|---|
| Time | Catalyst | Conversion CO (%) | Selectivity CH4 (% mol C) | Selectivity C5+ (% mol C) |
| 2 hours | A* | 50 | n.a. | n.a. |
| 2 hours | B** | 10 | n.a. | n.a. |
| 24 hours | A* | 51 | 6.5 | 85.5 |
| 24 hours | B** | 45 | 8 | 82 |
| 1 week | A* | 50 | 7 | 84.5 |
| 1 week | B** | 44 | 8.5 | 81 |

*according to the invention
**comparative

The results obtained, set out in Table 4, illustrate the advantage of the reduction procedure of the Fischer-Tropsch catalyst in the presence of a reduction gas comprising an admixture of $H_2$ and CO. In this manner, the catalyst A reduced at low temperature (230° C.) and in the presence of synthesis gas, available in situ, in an item of equipment which is integrated in the schematic illustration of the Fischer-Tropsch method, has improved catalytic performance levels, both in terms of activity and selectivity. Furthermore, this catalyst is immediately operational.

Our invention allows the provision of such a catalyst activated in the presence of synthesis gas for starting the Fischer-Tropsch unit and also for all the additions of catalyst during operation of the Fischer-Tropsch synthesis reactor (not illustrated in this example, but which can be produced as in Example 1).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding French application No. 11/03.861, filed Dec. 14, 2011, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for continuous production of hydrocarbons from synthesis gas in the presence of a catalyst, comprising a synthesis in which a synthesis gas is reacted in the presence of a catalyst in a Fischer-Tropsch synthesis reactor (4), comprising, at the same time as the synthesis, carrying out the following successively:
a) charging a catalyst precursor comprising cobalt oxide in a dedicated reduction reactor (2);
b) reducing the catalyst precursor charged in a) by placing it in contact with a reduction gas comprising hydrogen ($H_2$) and/or carbon monoxide (CO); and
c) introducing the catalyst reduced in b) into the synthesis reactor (4), wherein reduction of the catalyst precursor in the dedicated reduction reactor (2) is carried out at the actual site of the Fischer-Tropsch, synthesis reactor (4).

2. The method according to claim 1, comprising a prior starting sequence which includes the following:
d) charging at least a useful quantity Q of the catalyst precursor in the oxidized state in the reduction reactor;
e) reducing the useful quantity Q of the catalyst precursor in the oxidized state charged in d) in the presence of a reduction gas comprising carbon monoxide (CO) and/or hydrogen ($H_2$);
f) supplying the useful quantity Q of the catalyst in the state reduced in e) to the Fischer-Tropsch synthesis reactor.

3. The method according to claim 1, wherein the reduction gas which comprises an admixture of hydrogen ($H_2$) and carbon monoxide (CO) originates from a source of synthesis gas (1) which also supplies the synthesis reactor (4).

4. The method according to claim 3, comprising a prior processing of the synthesis gas upstream of reducing the catalyst precursor in order to modify the molar ratio $H_2/CO$ of the reduction gas which supplies the reduction reactor (2).

5. The method according to claim 1, wherein the reduction is carried out at a temperature between 200 and 500° C., at a total pressure between 0.1 and 5 MPa and under a gas flow between 0.1 and 20 Nl/h/g of catalyst to be processed.

6. The method according to claim 1, wherein the molar ratio $H_2/CO$ of the reduction gas of step b) is between 0.01 and 10.

7. The method according to claim 1, wherein the catalyst precursor includes a support which comprises an oxide of one or more of Al, Si, Ti, Zr, Ce, Cu, Zn, Ni, or Co.

8. The method according to claim 1, wherein the catalyst precursor further comprises one or more metals or metal oxide(s) of Cu, Mn, Ru, Pd, Pt, Re, or La.

9. The method according to claim 1, comprising at least one intermediate conditioning of the catalyst reduced in b), the conditioning operation being carried out before c) by placing the reduced catalyst in contact with a reduction gas which comprises carbon monoxide alone or an admixture of hydrogen and carbon monoxide.

10. The method according to claim 9, wherein the molar ratio $H_2/CO$ of the conditioning reduction gas is between 0.01 and 10.

11. The method according to claim 10, wherein the molar ratio $H_2/CO$ of the conditioning reduction gas is between 1 and 2.5.

12. The method according to claim 9, wherein the conditioning comprises a plurality of conditioning phases, each phase being carried out in the presence of a conditioning reduction gas which has a molar ratio $H_2/CO$ which is different from that of the preceding phase.

13. The method according to claim 9, wherein conditioning the catalyst is carried out in the reactor reducing the catalyst precursor.

14. The method according to claim 9, wherein conditioning the catalyst is carried out in a dedicated reactor which is different from the reactor reducing the catalyst precursor and different from the Fischer-Tropsch synthesis reactor.

15. The method according to claim 1, wherein the reduced catalyst is supplied to the Fischer-Tropsch synthesis reactor by a pressure change.

16. The method according to claim 2, comprising at least one intermediate conditioning of the catalyst reduced in e), the conditioning operation being carried out before f) by placing the reduced catalyst in contact with a reduction gas which comprises carbon monoxide alone or an admixture of hydrogen and carbon monoxide.

* * * * *